(12) United States Patent
Singh et al.

(10) Patent No.: US 6,391,279 B1
(45) Date of Patent: *May 21, 2002

(54) RADIOACTIVE SEEDS FOR BRACHYTHERAPY AND A PROCESS FOR MAKING THE SAME

(75) Inventors: Prahlad R. Singh, Arlington; Gerald P. Tercho, Lexington, both of MA (US); Jack N. Wentz, Nashua; Keith R. Olewine, Merrimack, both of NH (US)

(73) Assignee: Bristol-Myers Squibb Pharma Company, Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/191,672

(22) Filed: Nov. 13, 1998

Related U.S. Application Data

(60) Provisional application No. 60/065,993, filed on Nov. 14, 1997.

(51) Int. Cl.[7] .................... A61K 103/00; A61K 103/30
(52) U.S. Cl. .................... 424/1.29; 424/1.29; 424/1.33; 424/1.11; 600/1; 600/2; 600/3; 600/8
(58) Field of Search ................ 424/1.29, 422, 424/1.11, 1.33; 427/2.14; 600/1, 2, 3, 8

(56) References Cited

U.S. PATENT DOCUMENTS

| | | |
|---|---|---|
| 3,351,049 A | 11/1967 | Lawrence |
| 3,640,093 A | 2/1972 | Levene et al. |
| 3,923,843 A | 12/1975 | Wulff |
| 4,323,055 A * | 4/1982 | Kubiatowicz ............... 128/1.2 |
| 4,410,501 A | 10/1983 | Taramasso et al. |
| 4,510,924 A | 4/1985 | Gray |
| 4,702,228 A | 10/1987 | Russell, Jr. et al. |
| 4,784,116 A | 11/1988 | Russell, Jr. et al. |
| 4,937,216 A | 6/1990 | Clerici et al. |
| 4,994,013 A * | 2/1991 | Suthanthiran et al. ......... 600/1 |
| 5,163,896 A * | 11/1992 | Suthanthiran et al. ......... 600/1 |
| 5,405,309 A | 4/1995 | Carden, Jr. |
| 5,525,563 A | 6/1996 | Thiele et al. |
| 5,575,749 A | 11/1996 | Liprie |
| 5,637,715 A | 6/1997 | Thiele et al. |
| 5,713,828 A * | 2/1998 | Coniglione .................... 600/1 |
| 5,759,945 A | 6/1998 | Carroll et al. |
| 5,997,463 A * | 12/1999 | Cutrer .......................... 600/8 |
| 6,007,475 A * | 12/1999 | Slater et al. ................... 600/8 |
| 6,099,458 A * | 8/2000 | Robertson ...................... 600/8 |
| 6,200,258 B1 * | 3/2001 | Slater et al. ................... 600/8 |

FOREIGN PATENT DOCUMENTS

| | | |
|---|---|---|
| CA | 2010038 | 2/1990 |
| DE | 3309669 | 3/1983 |
| DE | 19545042 | 12/1995 |
| EP | 0 292630 | 11/1988 |
| EP | 0634212 | 1/1995 |
| EP | 0734764 | 3/1996 |

OTHER PUBLICATIONS

Rustgi. *Am. Assoc. Phys. Med.*, vol. 19, No. 4, pp 927–931 (Jul./Aug. 1992).
Ching, *Precious Met.*, vol. 16, pp 129–139 (1992).
Thangaraj et al., *Zeolites*, vol. 12, No. 8, pp 943–950 (1992).
Tatsumi et al., *Chemical Abstracts*, vol. 128, No. 18, Abstract No. 222074 (1998).

* cited by examiner

*Primary Examiner*—Diana Dudash
*Assistant Examiner*—Shahnam Sharareh
(74) *Attorney, Agent, or Firm*—Maureen P. O'Brien; Peter L. Dolan

(57) ABSTRACT

Novel radioactive seeds for brachytherapy and a reproducible method of manufacturing the seeds is described, wherein the seeds contain either Pd-103 or I-125 disposed within a cured resin matrix.

25 Claims, No Drawings

RADIOACTIVE SEEDS FOR BRACHYTHERAPY AND A PROCESS FOR MAKING THE SAME

This application claims the benefit of U.S. Provisional Application No. 60/065,993 filed Nov. 14, 1997.

FIELD OF THE INVENTION

This invention relates generally to radioactive seeds for brachytherapy and a process for making the same. In particular, the present invention relates to radioactive seeds containing either Pd-103 or I-125 located within a cured resin matrix.

BACKGROUND OF THE INVENTION

Brachytherapy refers to the treatment of diseases, especially the treatment of tumors, including malignant tumors such as cancer, with radiation. Radioactive seeds (a.k.a., radioactive pellets, interstitial implants and discrete brachytherapy sources) are a well known means of delivering a radioactive source to a target. A variety of radioactive sources have been used, all with the goal of irradiating diseased tissue and minimizing irradiation of healthy tissue. Consequently, it is desirable to have a source which provides uniform radiation and which can be detected after implantation (i.e., X-ray). Thus, radioactive seeds often contain some type of X-ray marker to ensure their proper placement.

A number of different radioactive seeds are known to those of skill in the art. For example, U.S. Pat. No. 3,351,049 describes a radioactive seed which has a sealed container with a cavity (e.g., stainless steel or titanium), an isotope within the cavity (e.g., I-125), and a carrier for maintaining the isotope's uniform distribution within the cavity, and optionally, an X-ray visualizable means (e.g, gold and tungsten. U.S. Pat. No. 4,323,055 describes an improved seed wherein a carrier body which is an X-ray detectable silver or silver-coated rod coated with radioactive iodine is used.

U.S. Pat. No. 4,702,228 describes a seed for brachytherapy containing a Pd pellet. The Pd is enriched in Pd-102 so that the seed may be activated (i.e., Pd-103 is formed) by exposure to neutron flux. U.S. Pat. No. 5,405,309 depicts a seed containing an electroconductive support pellet, Pd-103 (carrier free) plated on the pellet and a biocompatible shell encapsulating the electroplated pellet. In order to overcome some of the problems of attaching a radioactive source to a carrier, U.S. Pat. No. 5,163,896 uses a metallic substrate having a radioactive-absorbing coating material containing polyamino acids (e.g., polytyrosine).

A number of problems exist with two of the currently used currently used radioactive sources Pd-103 and I-125. Sources like Pd-103 can be difficult to uniformly apply to a carrier. For example, when Pd-103 is plated onto a carrier, Pd-102 is used to enhance the plating process. Unfortunately, the presence of Pd-102 can attenuate a significant portion of the gamma rays emitted from Pd-103. Seeds containing either Pd103 or I-125 are generally prepared by coating the source onto a carrier and then manually assembling the seed. Such manual assembly can lead to numerous errors when a X-ray marker needs to be included. In addition, there is always an issue of operator exposure when a radioactive source is being handled.

Due to the importance of brachytherapy and the numerous inefficiencies of current radioactive seed technology, it is thus desirable to find new radioactive seeds and reproducible ways of manufacturing radioactive seeds which provide uniform output of seeds.

SUMMARY OF THE INVENTION

Accordingly, one object of the present invention is to provide a novel radioactive seed.

It is another object of the present invention is to provide a process for manufacturing radioactive seeds.

These and other objects, which will become apparent during the following detailed description, have been achieved by the inventors discovery that a cured mixture of a resin and a radionuclide can be conveniently and reproducibly prepared and used for brachytherapy.

DETAILED DESCRIPTION OF PREFERRED EMBODIMENTS

[1] In a first embodiment, the present invention provides a novel seed, comprising:
   (a) a biocompatible capsule having a hollow core; and,
   (b) a first length of a cured mixture disposed within the hollow core, the cured mixture, comprising:
      (bi) a resin, and
      (bii) a radionuclide suitable for brachytherapy.

[2] In preferred embodiment, the seed further comprises:
   (c) a second length of a cured mixture disposed within the hollow core; and,
   (d) a X-ray marker disposed within the hollow core, the X-ray maker being located between the first and second lengths of cured mixture.

[3] In a more preferred embodiment, the radionuclide is selected from Pd-103 and I-125.

[4] In an even more preferred embodiment, the radionuclide is Pd-103.

[5] In an even more preferred embodiment, the radionuclide is I-125.

[6] In another more preferred embodiment, the biocompatible capsule is comprised of a material selected from the group: titanium, aluminum, magnesium, and plastic.

[7] In an even more preferred embodiment, the biocompatible capsule is comprised of titanium.

[8] In another more preferred embodiment, the resin is selected from epoxy, polyurethane, polyimide, and polyamide.

[9] In another more preferred embodiment, each length of cured mixture is surrounded by plastic tubing.

[10] In another more preferred embodiment, the X-ray marker is selected from silver, gold, tungsten, and lead.

[11] In a second embodiment, the present invention provides a novel process for manufacturing a seed, comprising:
   (1) blending a radionuclide suitable for brachytherapy and a resin to form a mixture;
   (2) transfering the mixture into plastic tubing;
   (3) curing the mixture;
   (4) cutting the tubing and cured mixture to a suitable length;
   (5) placing a cut length of cured mixture into a biocompatible capsule; and,
   (6) sealing the capsule.

[12] In another preferred embodiment, the radionuclide is selected from Pd-103 and I-125.

[13] In another preferred embodiment, the resin is selected from epoxy, polyurethane, polyimide, and polyamide.

[14] In another preferred embodiment, the biocompatible capsule is comprised of a material selected from the group: titanium, aluminum, magnesium, and plastic.

[15] In another more preferred embodiment, the biocompatible capsule is comprised of titanium.

[16] In another preferred embodiment, the tubing is selected from polyethylene, polypropylene, polyvinyl chloride, polyvinyl acetate, polyimide, polyamide, polytetrafluoroethylene and polyvinylidene chloride.

[17] In another preferred embodiment, step (4), comprises:

(4i) removing the tubing from the cured mixture; and, (4ii) cutting the cured mixture to a suitable length.

[18] In another preferred embodiment, step (5), comprises:

(5i) placing a first cut length of cured mixture into a biocompatible capsule;

(5ii) placing a X-ray marker into the capsule; and, (5iii) placing a second cut length of cured mixture into the capsule, whereby the X-ray marker is positioned between the first and second lengths of cured mixture.

[19] In another preferred embodiment, the X-ray marker is selected from silver, gold, tungsten, and lead.

[20] In a third embodiment, the present invention provides a novel seed, comprising:

(a) a first biocompatible polymer in the shape of a seed; and, (b) a radionuclide suitable for brachytherapy, the radionuclide being present within the first biocompatible polymer.

[21] In another preferred embodiment, the seed further comprises (c) a X-ray marker disposed within the first biocompatible polymer material.

[22] In another preferred embodiment, the seed further comprises:

(d) a second biocompatible polymer encapsulating the first biocompatible polymer.

[23] In a more preferred embodiment, the radionuclide is selected from Pd-103 and I-125.

[24] In another more preferred embodiment, the X-ray marker is selected from silver, gold, tungsten, and lead.

[25] In another more preferred embodiment, the first and second biocompatible polymers are independently selected from polyimide, polyamide, epoxy and polyisocyanurate.

[26] In a fourth embodiment, the present invention provides a novel process for manufacturing a seed, comprising:

(1) blending a radionuclide suitable for brachytherapy and a resin to form a mixture;

(2) transfering the mixture into a biocompatible capsule;

(3) curing the mixture; and, (4) sealing the capsule.

[27] In another preferred embodiment, the radionuclide is selected from Pd-103 and I-125.

[28] In another preferred embodiment, the resin is selected from epoxy, polyurethane, polyimide, and polyamide.

[29] In another preferred embodiment, the biocompatible capsule is comprised of a material selected from the group: titanium, aluminum, magnesium, and plastic.

[30] In another more preferred embodiment, the biocompatible capsule is comprised of titanium.

DESCRIPTION

Biocompatible Capsule

Biocompatible, as used herein, is intended to indicate a material which is medically acceptable to be placed within a patient for a sufficient length of time to affect brachytherapy treatment. A biocompatible capsule, as used herein is a sealed tube encapsulating (i.e., housing) the other components of the seed. The biocompatible material is preferably of low atomic weight, for example, titanium, aluminum, magnesium, or plastic. The plastic could be selected from a variety of polymers, including polyethylene terphthalate, polyimide, polyamide, polytetrafluoroethylene polycarbonate, and ethylene-tetrafluoroethylene copolymer. It is preferred that the capsule have an open end and a closed end. The capsule is preferably sealed with a suitable end cap using mechanical techniques such as swaging or laser/electron beam welding or by using an equally impervious sealing agent, adhesive, glue or similar sealant.

The size of the capsule will depend on its therapeutic application and its contents. Preferably, the capsule is no longer than about 0.180 in. The outer diameter is preferably about 0.32 in. The inner diameter is preferably about 0.28 in. The wall thickness of the capsule is preferably about 0.002 in. In order to seal the capsule, an end plug is usually needed. This plug is preferably about 0.028 in. long and has an inner diameter of about 0.026 in. and outer diameter about 0.028 in.

When the capsule contains two lengths of cured mixture and an X-ray marker, it is preferred that each length of cured mixture is from about 0.025–0.048 in. long with a diameter of about 0.022–0.025 in. When the capsule contains one length of cured mixure, it is preferred that the mixture is from about 0.075–0.110 in. long and from about 0.022–0.025 in. in diameter.

Alternatively, the capsule can be made of biocompatible polymer material impervious to dissolution or digestion by body fluids or tissue (e.g., polyimide such as Kapton, polyamide such as Nylon, epoxy resin, polyisocyanurate or other polymeric materials), preferably epoxy resin. In this embodiment, the biocompatible polymer material will contain a radionuclide, and preferably contains a X-ray marker. The capsule in this embodiment is preferably no longer than 0.180 in. and about 0.032 in. wide. The radionuclide is, preferably, palladium-103, iodine-125, erbium-165, erbium-169 or ruthenium-97, and is uniformly blended, mixed, or dispersed in the biocompatible polymer material. The preferred blending mechanism is to react the nuclide or its complex chemically with the polymer material in order to achieve a uniform dispersion. The X-ray marker, when present, is preferably sealed inside the polymer material. The term "sealed" is intended to mean that the X-ray marker is not present on the surface of the seed. In order to ensure that there is no direct contact between the patient, the radionuclide or X-ray marker, it may be desirable to overcoat the seed with a biocompatible polymeric resin which contains no radionuclide or X-ray marker. The biocompatible polymer material in this embodiment could be encased within the tubing described below.

X-ray Marker

The X-ray marker is comprised of a X-ray detectable element, preferably, silver, gold, lead, or tungsten. The X-ray marker is generally of a shape which conveniently fits inside the desired capsule, e.g., cylindrical or spherical. Preferably, the X-ray marker is cylindrical in shape and sized to fit the cure tubing (described below). The X-ray marker is of sufficient size that it is visualizable once inserted within a patient. The cylinder (i.e., wire) must be large enough to be visible with X-rays, preferably about 0.005–0.010 in. In the case of silver and gold marker, the cured material could be cut and directly used for implantation without overcoat. Lead and tungsten would require an overcoat to seal the ends of the marker after cutting to limit exposure of such material to a patient. It is preferred that the X-ray marker, when present, is located between the two lengths of cured resin. The X-ray marker can also be a wire within the biocompatible polymer material. When it is a wire, the X-ray marker is preferably about 0.025–0.042 in. long and has a diameter of about 0.010–0.025 in. When spherical, the X-ray marker is preferably has a diameter of about 0.010–0.025 in.

Resin

Resin, as used herein, is intended to refer to a curable material which can be blended with a radionuclide. Resin is intended to include resinous materials as well as polymeric materials. The desired resin is of the nature which allows for blending with a radionuclide to obtain a homogeneous mixture and is curable by means known to those of skill in the art. The type of resin selected will depend upon the radionuclide and the desired curing method. A variety of different resins can be used, e.g., epoxy, polyurethane, polyimide, and polyamide. Other resins can include polysulfones, urea-formaldehyde, polyester, silicone, polystyrene-olefin copolymers, polystyrene-vinyl toluene copolymers, phenyl-methyl silicone resin and phenol-formaldehyde resins.

In order to obtain a homogeneous dispersion of the radionuclide in the resin structure, it may be desirable to chemically bond the radionuclide to the resin. Radionuclide-resin bonding can be achieved by utilizing active functionalities in the resin, such as chlorides, hydroxyl groups, carboxyls, amines, amides, and imide functional groups. Bonding can also be achieved by using resins with unsaturated double bond linkages.

Depending on the desired curing technique, other components may be present besides the resin and radionuclide. These components include catalysts, hardeners, or a mixture of both.

Radionuclides

A variety of radionuclides are known to be useful in brachytherapy. Preferably, the radionuclide is selected from, palladium-103, iodine-125, erbium-165, erbium-169 or ruthenium-97. The radionuclide may be in its elemental or non-elemental forms. A variety of different groups can be associated with the radionuclide. Such groups are preferably selected from amines, chlorides, bromides, iodides, cyanides, nitrides, sulfates, isonitriles, phosphites, organic sulfides, tertiary phosphines and their analogs containing alkyl or aryl groups.

For example, I-125 may be blended directly in its elemental form, or as iodide, iodate, hypoiodate, or other ionic forms, or in the form of compounds such as aliphatic or aromatic iodo labeled compounds. Iodide, or iodobenzene could be selected if the polymer system was a basic form of epoxy resin.

The range of desired activity is about 0.5 to 4.0 mCi per capsule. It is to be recognized that this range will depend on the isotope chosen and the therapeutic application.

Process

The process for preparing the present seeds involves (a) blending a desired radionuclide with a desired resin to obtain a homogeneous mixture; (b) transfering the homogeneous mixture into tubing; (c) curing the mixture; (d) cutting the cured mixture to a desired length; (e) placing a cut length of the cured mixture into a suitable biocompatible capsule; and (f) sealing the capsule.

One of skill in the art would recognize that blending of the radionuclide and resin can be achieved by numerous well known means. The aim of the blending step is to achieve a homogeneous mixture of radionuclide and resin. Homogeneous, as used herein, is intended to mean a mixture wherein the radionuclide is nearly evenly (i.e., uniformly) distributed throughout the resin. As indicated above, the radionuclide can be in its elemental or non-elemental form and the resin may contain active functionalities to aid in dispersion of the radionuclide.

Once a homogeneous mixture is obtained, the mixture is then transferred into tubing. The resin may be transfered into the tubing using a vacuum to draw it, pumping (centrifugal or peristaltic), or by pressurizing the headspace over the resin in the reservoir containing the resin. Other methods of transfering resin mixtures can also be used.

The tubing used in the present process is thin walled plastic tubing and can be of any tubing capable of containing the resin, such as polyethylene, polypropylene, polyvinyl chloride, or polyvinyl acetate; or it can be of the thermoset variety such as polyimide, polamide polytetrafluoroethylene or polyvinylidene chloride. Thin walled, as used herein, generally means less that about 0.001 in. It is preferred to use the thinnest possible wall thickness in order to limit attenuation. The inner diameter of the tubing is preferably from about 0.020–0.024 in, with a wall thickness of about 0.0003–0.001 in.

Once the mixture has been transferred into the tubing, it is preferred that both ends of the tubing are clamped prior to curing. The resin-radionuclide blend can be cured using heat or ultraviolet radiation. In addition, curing can be achieved through use of room temperature catalysts or hardeners blended with a resin curable in this fashion (e.g., epoxy, polyurethane, polyester, and silicones). Room temperature curing is preferred for volatile radionuclides (e.g., I-125) in order to reduce the volatility.

The cured mixture can then be cut to specific lengths depending on the activity requirements of the therapy. The activity per unit length of cured mixture can be determined prior to cutting to aid in determining the required length. The tubing surrounding the cured mixture can be left in place or removed. The polymer tubing can be mechanically removed from the cured radioactive matrix prior to cutting. This is accomplished by drawing the epoxy matrix filled tubing through a longitudinal or spiral cutting die, then mechanically stripping the tubing from the active matrix. The cured active matrix stripped of the tubing is then cut to a desired length.

The seed is then assembled by placing a first length of cured mixture into a biocompatible capsule. If desired, a second length of cured mixture may be placed in the capsule. Also, if desired, a X-ray marker may be placed in the capsule, between the first and second lengths of cured mixture.

Assembly of the small components of the seed could be done manually, however the resin matrix can be cut to a specific activity target and presented in a good repeatable orientation for an automatic pick and place assembly machine. The biocompatible capsule tubing would be placed in close tolerance tooling fixtures. The X-ray marker and the end cap for sealing the capsule could be presented using a tape or tray presentation required by the machine. The assembly machine would be equipped with machine vision to allow it to locate fixtures and components and properly assemble them. Machine vision would also allow for automated inspection of the seeds in the assembly process. This would be a considerable advantage over the slow, error-prone manual methods which have previously be used.

Once the seed is assembled, the biocompatible capsule is sealed by placing an end cap over the open end. A laser welder with machine vision would seal the capsules. The capsules would be presented to the welder in the same fixtures used in assembly. The welder would be equiped with machine vision to allow it to locate fixtures and components for welding. Machine vision would also allow for automated inspection of the seeds in the sealing process. Other methods of sealing capsules, which are well known to those of skill in the art, could also be used.

Alternatively, the resin/radionuclide blend can be dispensed directly into the biocompatible capsule prior to curing. The mixture would then be cured in the capsules, which are then sealed with end plugs by laser welding or with adhesive sealant. No cutting is required for this process.

Other features of the invention will become apparent in the course of the following descriptions of exemplary embodiments which are given for illustration of the invention and are not intended to be limiting thereof.

EXAMPLES

Example 1

A radioactive seed of the present invention may be prepared according to the following general process:
1. Prefill a reservoir with the resin and hardening agents.
2. Begin agitation.
3. Connect lot bottle of radionuclide.
4. Draw a slight vacuum on the reservoir to draw the radionuclide into the reservoir.
5. Close the vent to the lot bottle and draw cold resin into the lot bottle to rinse it. After rinsing the lot bottle the resin is drawn into the reservoir.
6. Vent the reservoir and remove the lot bottle.
7. Continue agitation until a homogenous mixture is obtained.
8. Open the drain valve on the reservoir and transfer the resin into a length of thin walled tubing attached to the drain.
9. Clamp the tubing at both ends and allow the resin to cure.
10. Samples of the tubing are taken to determine the specific activity per unit length of the resin.
11. The resin is cut to length to meet the activity requirements for specific seeds and the seed is assembled.
12. After assembly, the assembled seeds are sealed.
13. A QC Mil Standard check is performed on the assembled seeds for activity, leak checking, etc.

Example 2

A blend of resin and radionuclide will be pumped or drawn from the reservoir through a valved fitting on the bottom of the reservoir into a length of thin wall polymer tubing connected to this fitting. The blended resin in the polymer tubing will then be cured using heat or ultraviolet radiation or through use of room temperature catalysts or hardeners blended with the epoxy resin. A preliminary assay will be performed to ensure proper matrix pellet content. The matrix will be cut into pellets that are loaded automatically into titanium capsules, along with the chosen X-ray marker. One end of the capsule will have been previously sealed. The end plugs will then be automatically inserted and laser welded into the capsules. The sealed capsules, or seeds will be leak tested and assayed for activity content.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A seed, comprising:
   (a) a biocompatible capsule having a hollow core;
   (b) a first length of a cured mixture disposed within the hollow core, the cured mixture, comprising:
       (bi) a cured resin, and
       (bii) a radionuclide suitable for brachytherapy;
   (c) a second length of a cured mixture disposed within the hollow core; and,
   (d) an X-ray marker disposed within the hollow core, the X-ray marker being located between the first and second lengths of cured mixture;
   wherein each length of cured mixture is surrounded by thin walled plastic tubing.

2. A seed according to claim 1, wherein the radionuclide is selected from Pd-103 and I-125.

3. A seed according to claim 1, wherein the biocompatible capsule is comprised of a material selected from titanium, aluminum, magnesium, and plastic.

4. A seed according to claim 1, wherein the cured resin is selected from epoxy, polyurethane, polyimide, and polyamide.

5. A seed according to claim 1, wherein the X-ray marker is selected from silver, gold, tungsten, and lead.

6. A process for manufacturing a seed, comprising:
   (1) blending a radionuclide suitable for brachytherapy and a curable resin to form a homogenous mixture;
   (2) transferring the homogenous mixture into thin-walled plastic tubing;
   (3) curing the homogenous mixture in the thin-walled plastic tubing;
   (4) cutting the thin-walled plastic tubing and cured homogenous mixture to a suitable length;
   (5) placing a first cut length of cured homogenous mixture into a biocompatible capsule;
   (6) placing a X-ray marker into the capsule;
   (7) placing a second cut length of cured homogenous mixture into the capsule, whereby the X-ray marker is positioned between the first and second lengths of homogenous cured mixture; and
   (8) sealing the capsule.

7. A process according to claim 6, wherein the radionuclide is selected from Pd-103 and 1-125.

8. A process according to claim 6, wherein the curable resin is selected from epoxy, polyurethane, polyimide, and polyamide.

9. A process according to claim 6, wherein the biocompatible capsule is comprised of a material selected from titanium, aluminum, magnesium, and plastic.

10. A process according to claim 6, wherein the tubing is selected from polyethylene, polypropylene, polyvinyl chloride, polyvinyl acetate, polyimide, polyamide, polytetrafluoroethylene and polyvinylidene chloride.

11. A process according to claim 6, wherein the X-ray marker is selected from silver, gold, tungsten, and lead.

12. A seed, comprising:
(a) a first biocompatible polymer in the shape of a seed;
(b) a radionuclide suitable for brachytherapy, the radionuclide being present within the first biocompatible polymer;
(c) an X-ray marker disposed within the first biocompatible polymer material; and
(d) a second biocompatible polymer encapsulating the first biocompatible polymer;

wherein the first and second biocompatible polymers are independently selected from polyimide, polyamide, epoxy and polyisocyanurate.

13. A seed according to claim 12, wherein the radionuclide is selected from Pd-103 and I-125.

14. A seed according to claim 12, wherein the X-ray marker is selected from silver, gold, tungsten, and lead.

15. A seed according to claim 12 wherein the radionuclide is selected from Pd103 and I-125.

16. A seed according to claims 12 wherein the X-ray marker is selected from silver, gold, tungsten, and lead.

17. A seed according to claim 1, wherein the thickness of the thin-walled plastic tubing is less than about 0.001 inch.

18. A seed according to claim 1, wherein the thickness of the thin-walled plastic tubing is between about 0.0003 to about 0.001 inch.

19. A seed according to claim 1, wherein the inner diameter of the thin-walled plastic tubing is from about 0.020 to about 0.024 inch.

20. A seed according to claim 1, wherein the thin-walled plastic tubing comprises polyethylene, polypropylene, polyvinyl chloride, or polyvinyl acetate.

21. A seed according to claim 1, wherein the thin-walled plastic tubing comprises a thermosetting plastic.

22. A seed according to claim 21, wherein the thermosetting plastic is selected from the group consisting of polyimide, polyamide, polytetrafluoroethylene and polyvinylidene chloride.

23. A process according to claim 6, wherein the thickness of the thin-walled plastic tubing is less than about 0.001 inch.

24. A process according to claim 6, wherein the thickness of the thin-walled plastic tubing is between about 0.0003 to about 0.001 inch.

25. A process according to claim 6, wherein the inner diameter of the thin-walled plastic tubing is from about 0.020 to about 0.024 inch.

* * * * *